(12) United States Patent
Carson et al.

(10) Patent No.: US 7,745,492 B2
(45) Date of Patent: *Jun. 29, 2010

(54) CARBOXAMIDO OPIOID COMPOUNDS

(75) Inventors: John R. Carson, Norristown, PA (US); Philip M. Pitis, North Wales, PA (US)

(73) Assignee: Janssen Pharmaceutical, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/182,462

(22) Filed: Jul. 30, 2008

(65) Prior Publication Data

US 2008/0280990 A1    Nov. 13, 2008

Related U.S. Application Data

(63) Continuation of application No. 11/766,892, filed on Jun. 22, 2007, now abandoned, which is a continuation of application No. 11/126,771, filed on May 11, 2005, now Pat. No. 7,244,866.

(60) Provisional application No. 60/571,298, filed on May 14, 2004.

(51) Int. Cl.
*A61K 31/165* (2006.01)

(52) U.S. Cl. ...................... 514/620; 564/164

(58) Field of Classification Search ............... 564/164; 514/620

See application file for complete search history.

(56) References Cited

U.S. PATENT DOCUMENTS

| 6,057,371 A | 5/2000 | Glennon |
| 6,071,970 A | 6/2000 | Mueller et al. |
| 6,248,737 B1 | 6/2001 | Buschmann et al. |
| 7,244,866 B2 * | 7/2007 | Carson et al. ............ 564/164 |
| 2005/0065120 A1 | 3/2005 | Christoph et al. |

FOREIGN PATENT DOCUMENTS

| CA | 2480038 A1 | 10/2003 |
| WO | WO 03/048113 A1 | 6/2003 |

OTHER PUBLICATIONS

Bidlack, J. M. et al., "8 Carboxamidocyclazocine: A Long-Acting, Novel Benzomorphan." *J. Pharm. & Exp. Thera.*, 2002, vol. 302, No. 1.

U. Klotz: "Tramadol—the Impact of its Pharmacokinetic and Pharmacodynamic Properties on the Clinical Management of Pain". Arzneim. -Forsch./Drug Res., vol. 53, No. 10, 2003, pp. 681-687, XP001207583.

Wentland, M. P. et al., "8-Carboxamidocyclazocine Analogues: Redefining the Structure-Activity Relationships of 2,6-Methano-3-benzazocines." *Bioorg. & Med. Chem. Lett.*, 2001, pp. 623-626, vol. 11.

Wentland, M. P. et al., "3-Carboxamido Analogues of Morphine and Naltrexone: Synthesis and Opioid Receptor Binding Properties." *Bioorg. & Med. Chem. Lett.*, 2001, pp. 1717-1721, vol. 11.

Zhang, A. et al. "10-Ketomorphinan and 3-Substituted-3-desoxymorphinan Analogues as Mixed k and y Opioid Ligands: Synthesis and Biological Evaluation of their Binding Affinity at Opioid Resceptors", J. Med. Chem., vol. 47, No. 1, Jan. 1, 2004, XP002350135.

Zhang, Z., et al., "Research Progress on a Novel Analgesic Drug Tramadol Hydrochloride", China Pharmacist, vol. 2, No. 6, 1999, pp. 290-291 (English Translation attached.).

* cited by examiner

*Primary Examiner*—Shailendra Kumar

(57) ABSTRACT

This invention is directed to carboxamido opioid compounds pharmaceutically useful as agents for treating or modulating a central nervous system disorder and methods for treating or modulating a central nervous system disorder.

4 Claims, 4 Drawing Sheets

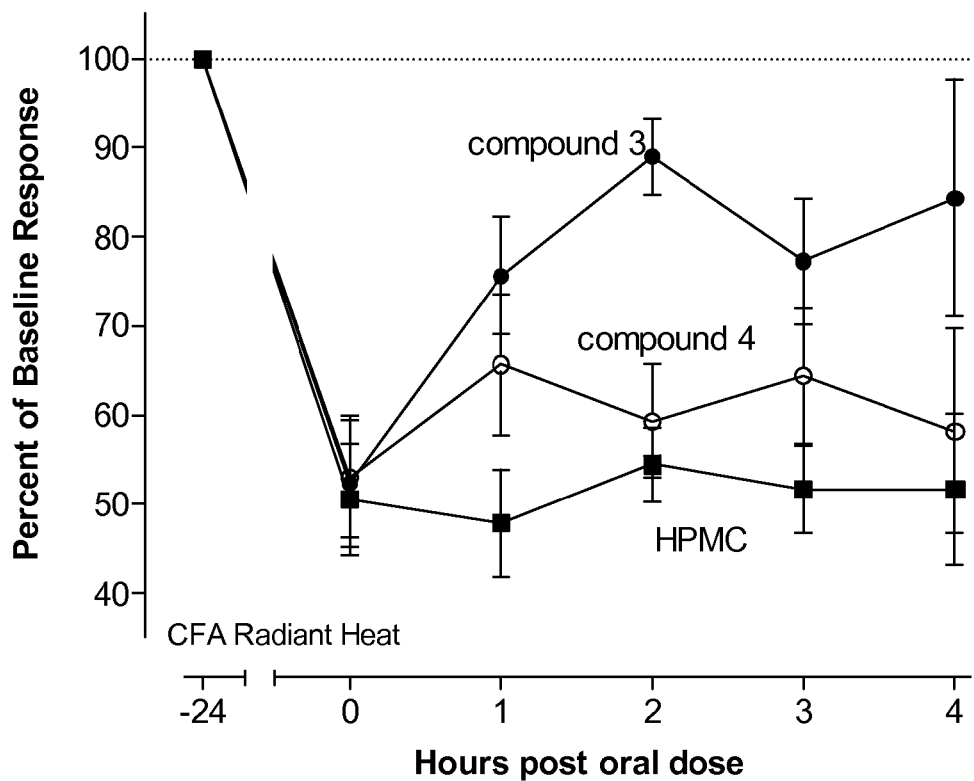
Figure 1. Antihyperalgesic effect of Compounds 3 and 4 in a rat CFA radiant heat model of inflammatory pain Figure 2. Analgesic effect of Compound 3 in a spinal nerve ligation (SNL) model of neuropathic pain.
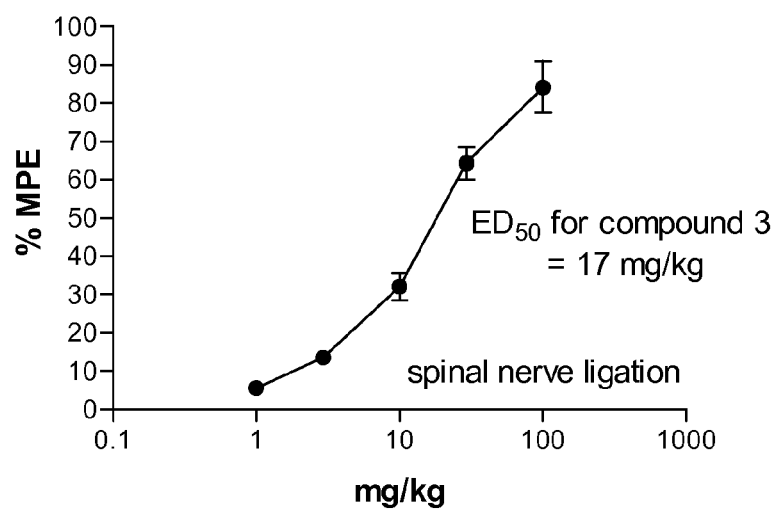

Figure 3. Study of the development of tolerance to the antiallodynic effect of Compound 3
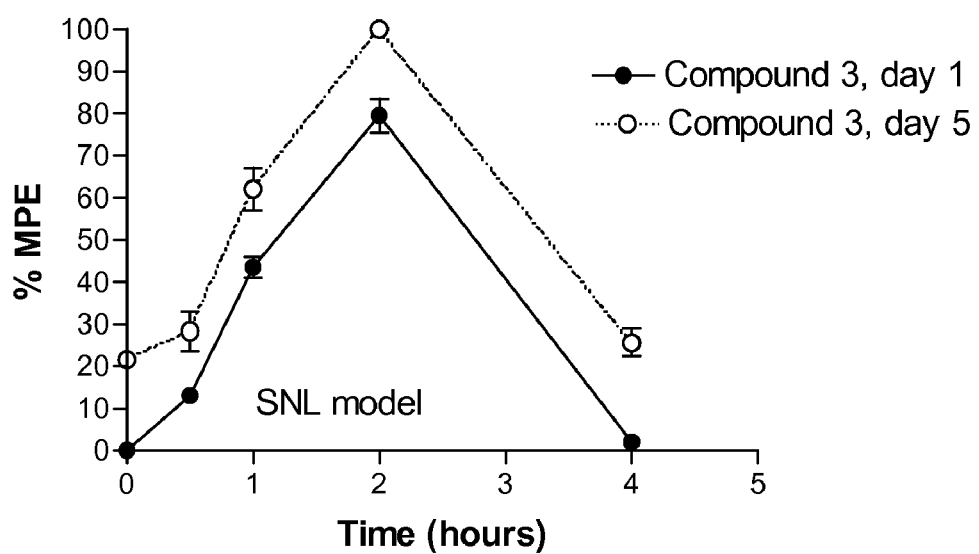

Figure 4. Study of the development of tolerance to the antiallodynic effect of morphine
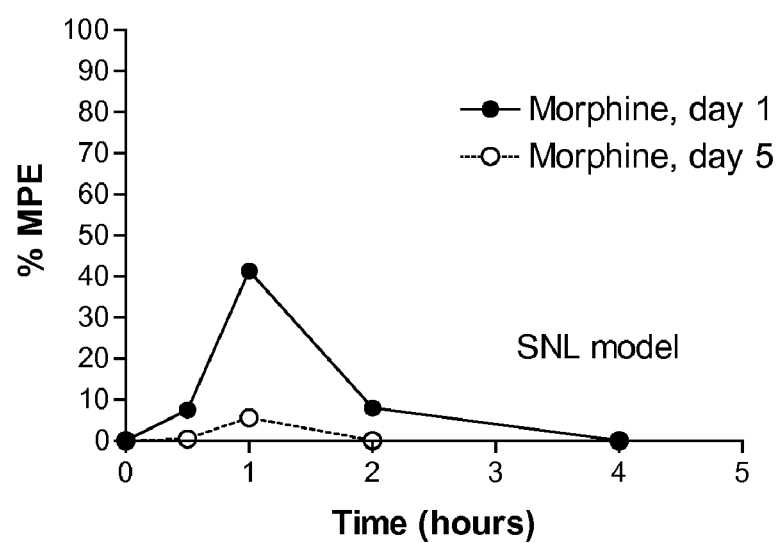

CARBOXAMIDO OPIOID COMPOUNDS

CROSS-REFERENCE TO RELATED APPLICATIONS

This is a continuation of application Ser. No. 11/766,892, filed Jun. 22, 2007, now abandoned which is a continuation of U.S. application Ser. No. 11/126,771, filed May 11, 2005, which has issued as U.S. Pat. No. 7,244,866 as of Jul. 17, 2007, which claims priority to U.S. Provisional Patent Application No. 60/571,298, filed May 14, 2004, which is hereby incorporated by reference in its entirety.

STATEMENT REGARDING FEDERALLY SPONSORED RESEARCH OR DEVELOPMENT

The research and development of the invention described below was not federally sponsored.

BACKGROUND OF THE INVENTION

Tramadol hydrochloride, (1RS, 2RS)-2-(dimethylamino)-methyl-1-(3-methoxyphenyl)-cyclohexanol HCl (tramadol), is a centrally-acting analgesic that has an unexpected distinction from morphine, the prototype pure opioid analgesic. Although tramadol was introduced into clinical practice in the 1970s without expectation of mechanistic differences from opiates, the data gathered to date in preclinical studies, clinical trials, epidemiological reports, and widespread use in patients indicate that a differentiation is appropriate. Tramadol is an atypical centrally acting analgesic in that its efficacy appears to be attributable to multiple mechanisms of action. The compound and its enantiomers bind with weak affinity to rodent and human μ-opioid receptors and with less affinity for δ- or κ-Opioid receptors. Tramadol's O-desmethyl metabolite binds with higher affinity than the parent compound, but still with much lower affinity than morphine. Thus, activation of μ-opioid receptors appears to be one of the components of tramadol's mechanism of action, but insufficient on its own to explain tramadol's antinociceptive and analgesic potency and efficacy.

A second, non-opioid component is suggested by several observations that include the incomplete naloxone reversibility in most animal models and in human trials; and, the attenuation of its antinociceptive or analgesic effect by non-opioid antagonists. Hence, the results are consistent with dual contributions, opioid and non-opioid, with the predominant contribution perhaps being dependent upon the species, route of administration, or particular nature of the pain. The source of the dual mechanisms has been hypothesized to arise from the different pharmacologies of the two enantiomers of tramadol, one being more opioid-like than the other.

Analgesics that operate via the μ-opioid receptor are typically phenols and phenol ethers. They frequently suffer from the drawback that they are metabolically inactivated by conversion to glucuronides, which are rapidly excreted. The carboxamide group has been found to be an effective bioisosteric surrogate for the phenol group in certain benzomorphans and morphinans, which has led to a series of opioids with a superior biological lifetime (Wentland, M. P. et al. *Bioorg. Med. Chem. Lett.* 2001, 11(5), 623-6; Wentland, M. P. et al. *Bioorg. Med. Chem. Lett.* 2001, 11(13), 1717-1721; Bidlack, Jean M. et al. *J. Pharmacol. Exp. Ther.*, 2002, 302(1), 374-380).

The preparation of certain 1-aryl-(2-dialkylaminomethyl) cycloclohexan-1-ols is disclosed in PCT application WO 03/080557 (CA2480038), issued Oct. 10, 2003 (Sundermann, B. et al, Grünenthal GMBH Assignee.). A genus of tramadol analogs is disclosed in PCT application WO 03/048113, issued Jun. 12, 2003 (Senanayake, C. H. et al., Seprecor Assignee).

Thus there is a need to address the metabolic inactivation of tramadol that occurs through the conversion of its hydroxy metabolite to the corresponding glucuronide. The present invention replaces the methoxy substituent of tramadol with a carboxamido group.

SUMMARY OF THE INVENTION

The present invention provides carboxamido opioid compounds of Formula (I):

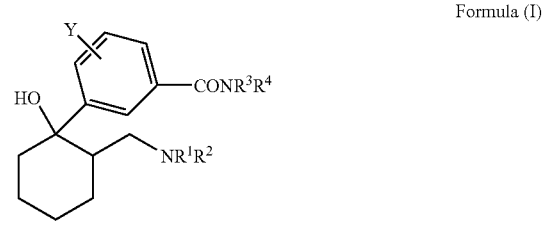

Formula (I)

wherein:
$R^1$ and $R^2$ are independently selected from the group consisting of hydrogen, lower alkyl, and alkyldiyl wherein $R^1$ and $R^2$ are taken together with the atoms to which they are attached to form a monocyclic ring;

$R^3$ and $R^4$ are independently selected from the group consisting of hydrogen, lower alkyl, $C_{3-7}$cycloalkyl, and alkyldiyl wherein $R^3$ and $R^4$ are taken together with the atoms to which they are attached to form a monocyclic ring;

Y is hydrogen, lower alkyl, lower alkoxy, halogen, or trifluoromethyl;

and pharmaceutically acceptable enantiomers, diastereomers, tautomers, solvates and salts thereof.

BRIEF DESCRIPTION OF THE DRAWINGS

FIG. 1 shows the antihyperalgesic effect of Compounds 3 and 4 in a rat CFA radiant heat model of inflammatory pain.

FIG. 2 shows the analgesic effect of Compound 3 in a spinal nerve ligation (SNL) model of neuropathic pain.

FIG. 3 shows the results of a study of the development of tolerance to the antiallodynic effect of Compound 3.

FIG. 4 shows the results of a study of the development of tolerance to the antiallodynic effect of morphine.

DETAILED DESCRIPTION OF THE INVENTION

Embodiments of the present invention include those compounds of Formula (I) wherein $R^1$ and $R^2$ are independently selected from the group consisting of hydrogen and $C_{1-4}$alkyl.

Embodiments of the present invention include those compounds of Formula (I) wherein $R^1$ and $R^2$ are independently selected from the group consisting of hydrogen and methyl.

Embodiments of the present invention include those compounds of Formula (I) wherein $R^1$ and $R^2$ are each methyl.

Embodiments of the present invention include those compounds of Formula (I) wherein $R^3$ and $R^4$ are independently selected from the group consisting of hydrogen, $C_{1-4}$alkyl, $C_{3-7}$cycloalkyl, and $C_{1-4}$alkyldiyl wherein $R^3$ and $R^4$ are taken together with the atoms to which they are attached to form a monocyclic ring.

Embodiments of the present invention include those compounds of Formula (I) wherein $R^3$ and $R^4$ are independently selected from the group consisting of hydrogen, methyl, and cyclopropyl.

Embodiments of the present invention include those compounds of Formula (I) wherein $R^3$ and $R^4$ are each hydrogen.

Embodiments of the present invention include those compounds of Formula (I) wherein Y is hydrogen, $C_{1-4}$alkyl, $C_{1-4}$alkoxy, or halogen.

Embodiments of the present invention include those compounds of Formula (I) wherein Y is hydrogen, methyl, or methoxy.

Embodiments of the present invention include those compounds of Formula (I) wherein Y is hydrogen.

A further embodiment of the present invention includes those compounds of Formula (I) as their 1R, 2R/1S, 2S enantiomeric pair.

Exemplified compounds of the present invention include
3-[(1-RS, 2-SR)-2-[(dimethylamino)methyl]-1-hydroxycyclohexyl]-benzamide;
3-[(1-RS, 2-RS)-2-[(dimethylamino)methyl]-1-hydroxycyclohexyl]-benzamide;
(−)-3-[(1R, 2R)-rel-2-[(dimethylamino)methyl]-1-hydroxycyclohexyl]-benzamide;
(+)-3-[(1S, 2S)-rel-2-[(dimethylamino)methyl]-1-hydroxycyclohexyl]-benzamide;
3-[(1-RS, 2-RS)-2-[(dimethylamino)methyl]-1-hydroxycyclohexyl]-N,N-diethyl-benzamide;
N-cyclopropyl-3-[(1-RS, 2-RS)-2-[(dimethylamino)methyl]-1-hydroxycyclohexyl]-benzamide; and
3-[(1-RS, 2-RS)-2-[(dimethylamino)methyl]-1-hydroxycyclohexyl]-N-methylbenzamide.

The compounds of the present invention may also be present in the form of pharmaceutically acceptable salts. For use in medicine, the salts of the compounds of this invention refer to non-toxic "pharmaceutically acceptable salts" (*Ref. International J. Pharm.*, 1986, 33, 201-217; *J. Pharm. Sci.*, 1997 (Jan), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

Where the compounds according to this invention are chiral, they may accordingly exist as enantiomers. In addition, the compounds may exist as diastereomers. It is to be understood that all such stereoisomers and racemic mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Unless specified otherwise, the term "alkyl" refers to a saturated straight or branched chain consisting solely of 1-8 hydrogen substituted carbon atoms; preferably, 1-6 hydrogen substituted carbon atoms; and, most preferably, 1-4 hydrogen substituted carbon atoms.

Unless specified otherwise, the term "alkoxy" refers to a saturated straight or branched hydrocarbon chain alcohol radical derived by the removal of the hydrogen atom from the hydroxide oxygen of the alcohol. The hydrocarbon chain consists solely of 1-8 hydrogen substituted carbon atoms; preferably, 1-6 hydrogen substituted carbon atoms; and, most preferably, 1-4 hydrogen substituted carbon atoms.

The novel carboxamido opioid compounds of the present invention are useful μ-opioid receptor modulators. In particular, the instant carboxamido opioid compounds are μ-opioid receptor modulators, useful as analgesics. Furthermore, the instant carboxamido opioid compounds are μ-opioid receptor modulators useful as analgesics with improved pharmacokinetic properties. Examples of pain intended to be within the scope of the present invention include, but are not limited to, centrally mediated pain, peripherally mediated pain, structural or soft tissue injury related pain, progressive disease related pain such as cancer pain, neuropathic pain and acute pain such as caused by acute injury, trauma or surgery and chronic pain such as caused by neuropathic conditions, diabetic peripheral neuropathy, post-herpetic neuralgia, trigeminal neuralgia, post-stroke pain syndromes or cluster or migraine headaches. The utility of the instant compounds as μ-opioid receptor modulators can be determined according to the procedures described herein.

An embodiment of the invention is a pharmaceutical composition comprising one or more compounds of this invention in association with a pharmaceutically acceptable carrier. Another embodiment is a pharmaceutical composition made by mixing any of the compounds described above and a pharmaceutically acceptable carrier. A further embodiment is a process for making a pharmaceutical composition comprising mixing any of the compounds described above and a pharmaceutically acceptable carrier. Still another embodiment of the present invention is a method for treating pain modulated by a mu-opioid ligand.

In the method for treating pain modulated by a μ-opioid ligand there is administered to a subject in need thereof any of the compounds as defined herein in a therapeutically effective dose to modulate the μ-opioid receptor. The compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

Another embodiment of the invention is a method of treating pain in a subject already tolerant to one or more μ-opioid medications other than a compound or compounds as defined herein, which method comprises administering to the subject in need thereof any of the compounds as defined herein in a therapeutically effective dose to modulate the μ-opioid receptor. The compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

A therapeutically effective dose for use of the instant compounds or a pharmaceutical composition thereof comprises a dose range of from about 0.001 mg to about 1,000 mg, in particular from about 0.1 mg to about 500 mg or, more particularly from about 1 mg to about 250 mg of active ingredient per day for an average (70 kg) human. The carboxamido opioids described herein may be administered in a reduced dose relative to their hydroxy counterparts as permitted by their improved pharmacokinetic profile.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. Advantageously, compounds of the present invention may be administered in a single daily dose or the total daily dosage may be administered in divided doses of two, three or four times daily.

It is apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Compounds of this invention may be administered in any of the foregoing compositions and dosage regimens or by means of those compositions and dosage regimens established in the art whenever use of the compounds of the invention as mu-opioid receptor modulators is required for a subject in need thereof.

Abbreviations used in the instant specification, particularly the Schemes and Examples, are as follows:
Cpd or Cmpd=compound
d=day/days
DMF=dimethylformamide
DPPF=1,1'-bis(diphenylphosphino)ferrocene
EtOAc=ethyl acetate
EtOH=ethanol
h=hour/hours
HATU=O-(7-Azabenzotriazol-1-yl)-N,N,N',N'-tetramethyluronium hexafluorophosphate
M=molar
MeCN=acetonitrile
MeOH=methanol
min minutes
rt/RT room temperature
THF=tetrahydrofuran
TFA=trifluoroacetic acid
OTf=triflate
TEA=triethylamine General Synthetic Methods Representative compounds of the present invention can be synthesized in accordance with the general synthetic methods described above and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Representative compounds of the present invention may be synthesized by the methods illustrated in Scheme A. Cyclohexanone A1 may be elaborated using a Mannich reaction with formaldehyde and an amine of formula A2 to give a compound of formula A3, wherein $R^1$ and $R^2$ are as previously defined. A Y-functionalized aryl-magnesium reagent of formula A4, prepared according to the literature (Knochel, P. et al. Synlett, 2003, 6, 885-887), may be added to a ketone of formula A3 to give a compound of formula A5. Treatment of a compound of formula A5 with hydroxide anion provides carboxamido compounds of formula A6.

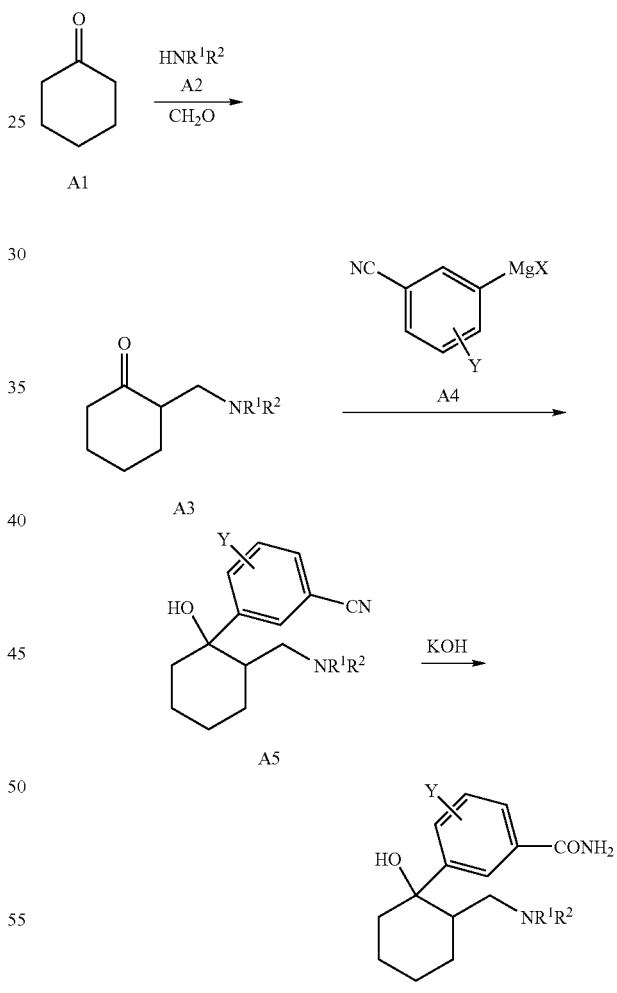

Scheme B shows an alternative synthetic route to compounds of the present invention. Starting with a Y-functionalized derivative of a tramadol metabolite, B1, which may be synthesized using methods known in the literature, treatment with triflic anhydride provides compounds of formula B2. Compounds

Scheme B

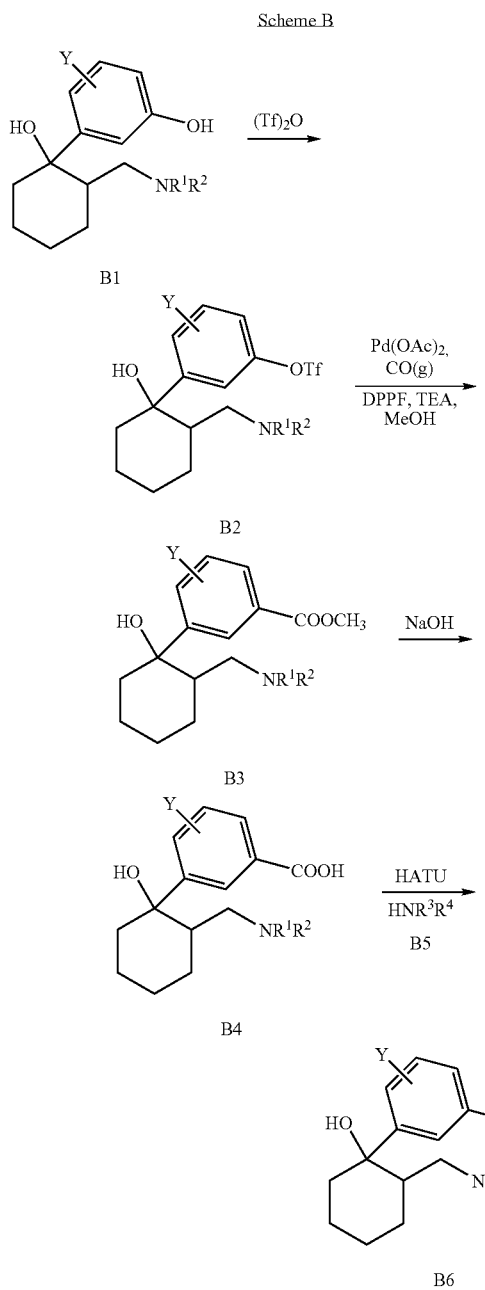

of formula B2 may be converted into compounds of formula B3 via a methoxycarbonylation using carbon monoxide gas bubbled through methanol in the presence of a palladium catalyst and a ligand such as (1,1'-bis(diphenylphosphino) ferrocene. Compounds of formula B3 may be saponified using hydroxide to form their corresponding carboxylic acid, B4. Compounds of formula B4 may be further elaborated to compounds of Formula (I) by coupling the carboxy group with an amine of formula B5 in the presence of an appropriate coupling agent, such as HATU in an aprotic solvent.

Diastereomers of the present invention may be separated by reverse phase or normal phase chromatography or by fractional crystallization. Racemic compounds of the present invention may be separated into their individual enantiomers using known methods from the literature (EP 786450).

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. Nuclear magnetic resonance (NMR) spectra for hydrogen atoms were measured in the indicated solvent with (TMS) as the internal standard on a Bruker Biospin, Inc. DPX-300 (300 MHz) spectrometer. The values are expressed in parts per million downfield from TMS. The mass spectra (MS) were determined on a Micromass Platform LC spectrometer or an Agilent LC spectrometer using electrospray techniques. Stereoisomeric compounds may be characterized as racemic mixtures or as separate diastereomers and enantiomers thereof using X-ray crystallography and other methods known to one skilled in the art. Specifically, chiral separations were performed by preparative HPLC using a Dynamic Axial Compression, type Prochrom LC50 column. Optical rotations were determined using a Perkin-Elmer Model 241 polarimeter. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Procedure A

3-[(2-Dimethylamino)methyl]-1-hydroxycyclohexyl]-benzonitrile

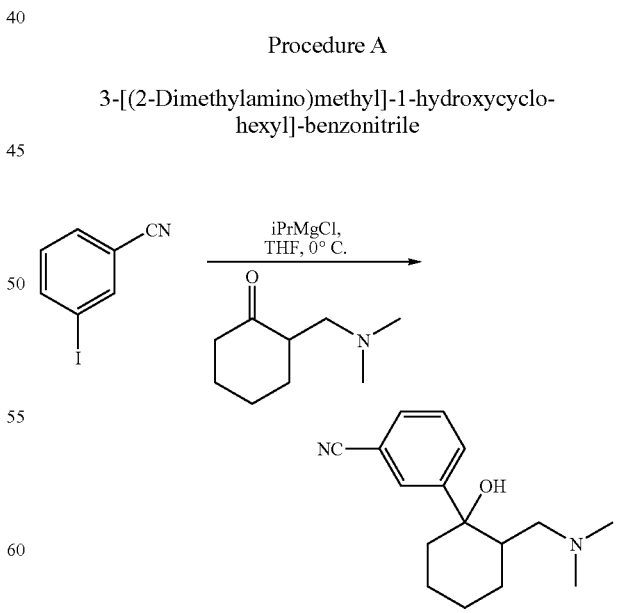

Isopropylmagnesium chloride (5.4 mL of a 2M solution in THF, 10.9 mmol) was added dropwise to a solution of 3-iodobenzonitrile (2 g, 8.7 mmol) in THF (20 mL) at 0° C. After stirring for 30 min, 2-dimethylaminomethyl-cyclohexanone was added and the ice bath removed. After 1 h, the reaction was quenched with saturated aqueous ammonium chloride (20 mL) and ethyl acetate (40 mL) was added. The organic phase was separated and then extracted with an aqueous solution of 1N hydrochloric acid (2×20 mL). The acid extracts were combined and then made basic with 2N sodium hydroxide solution. The basic solution was then extracted with chloroform (3×20 mL). The organic extracts were combined, dried ($K_2CO_3$), filtered, and concentrated under reduced pressure to afford 3-[(2-dimethylamino)methyl]-1-hydroxycyclohexyl]-benzonitrile as a mixture of four diastereomers (1.66 g, 73%).

Example 1

3-[(1-RS, 2-SR)-2-[(Dimethylamino)methyl]-1-hydroxycyclohexyl]-benzamide, Cpd 1

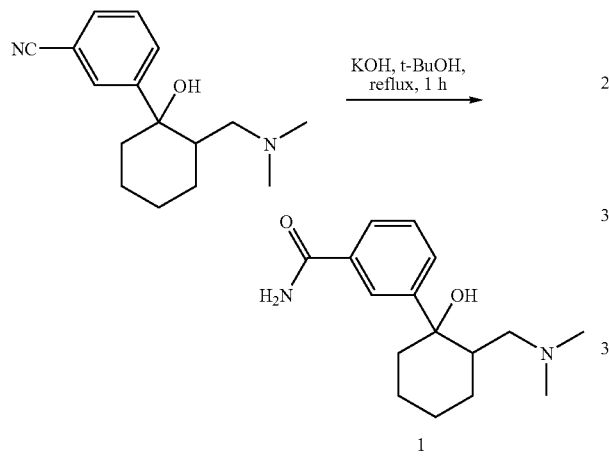

A sample of 3-[(2-dimethylamino)methyl]-1-hydroxycyclohexyl]-benzonitrile (Procedure A, 1.66 g, 6.4 mmol) as a mixture of diastereomers was dissolved in tert-butanol (20 mL), powdered potassium hydroxide (1.8 g, 32.1 mmol) was added, and the reaction was brought to reflux for 1 h. After cooling the reaction, chloroform (50 mL) and water (50 mL) were added. The organic layer was separated, dried ($K_2CO_3$), filtered, and concentrated to afford 3-[(2-dimethylamino)methyl]-1-hydroxycyclohexyl]-benzamide as a diastereomeric mixture (1.6 g, 93%). The mixture was purified on a reverse phase C-18 column with 0.5% ammonium acetate in water and acetonitrile as eluents. Compound 1, 3-[(1-RS, 2-SR)-2-[(dimethylamino)methyl]-1-hydroxycyclohexyl]-benzamide, eluted first. Next to elute was Compound 2, 3-[(1-RR, 2-SS)-2-[(dimethylamino)methyl]-1-hydroxycyclohexyl]-benzamide.

An alternative method for the separation of Compounds 1 and 2 uses a C-18 column and 0.01 M sodium sulfate in water (adjusted to pH 2.5 with sulfuric acid)/methanol: isocratic mixture 85/15, and washed with pure methanol between runs. The pure fractions of separated Cpd 2 and the pure fractions of separated Cpd 1 were separately but identically treated: the solvents were evaporated, and the resultant mixture (pure isomer+water+0.01M ammonium acetate in water (adjusted to pH=2.5 with sulfuric acid)) was injected on a water pre-flushed C-18 column to remove any salts. Subsequently, the pure diastereomeric mixture was flushed off the column with a gradient of water and methanol.

Example 2

3-[(1-RS, 2-RS)-[(2-Dimethylamino)methyl]-1-hydroxycyclohexyl]-benzamide, Cpd 2

The title compound eluted second from the separation described in Example 1: CIMS (M+H) m/z=277

Example 3

(−)-3-[(1 RS, 2R)-rel-[(2-Dimethylamino)methyl]-1-hydroxycyclohexyl]-benzamide, Cpd 3

The 3-[(1-RS, 2RS)-2-[(dimethylamino)methyl]-1-hydroxycyclohexyl]-benzamide was then resolved using a Chiralpak AD column with 100% acetonitrile as the eluent and with 100% ethanol for rinsing the column in between each injection, to afford (−)-3-[(1R, 2R)-rel-2-[(dimethylamino)methyl]-1-hydroxycyclohexyl]-benzamide (2.25 g): MS m/z 277.0 (MH+); $[\alpha]_D^{25}$ −33.5 (c 1, $CHCl_3$); Analytical reverse phase HPLC (gradient 10-90% MeCN, 0.1% aqueous TFA) $t_R$=1.52 min, ~99%; $^1$H NMR ($CDCl_3$) δ 1.35-1.43 (s, 1H), 1.55-1.65 (m, 2H), 1.66-1.68 (m, 3H), 1.74-1.79 (m, 1H), 1.88 (d, 1H, J=13 Hz), 2.02-2.05 (m, 3H), 2.18 (s, 6H), 2.43-2.46 (m 1H), 5.69 (s, 1H), 6.44 (s, 1H), 7.43 (t, 1H, J=7.7 Hz), 7.69-7.72 (m, 2H), 8.0 (s, 1H).

Example 4

(+)-3-[(1S, 2S)-rel-[(2-Dimethylamino)methyl]-1-hydroxycyclohexyl]-benzamide, Cpd 4

The second compound to elute from the resolution described in Example 3 was (+)-3-[(1S, 2S)-rel-2-[(dimethylamino)methyl]-1-hydroxycyclohexyl]-benzamide, (2.3 g), MS m/z 277 (MH+); $[\ ]_D^{25}$ +33.6 (c 1, $CHCl_3$); Analytical reverse phase
HPLC (gradient 10-90% MeCN, 0.1% aqueous TFA) $t_R$=1.49 min, ~99%; $^1$H NMR ($CDCl_3$) δ 1.35-1.43 (s, 1H), 1.55-1.65 (m, 2H), 1.66-1.68 (m, 3H), 1.74-1.80 (m, 1H), 1.88 (d, 1H, J=13.2 Hz), 2.02-2.06 (m, 3H), 2.18 (s, 6H), 2.43-2.45 (m 1H), 5.75 (s, 1H), 6.46 (s, 1H), 7.43 (t, 1H, J=7.7 Hz), 7.69-7.72 (m, 2H), 8.01 (s, 1H).

Procedure B

Trifluoromethanesulfonic acid 3-[(1-RS, 2-RS)-2-[(dimethylamino)methyl]-1-hydroxycyclohexyl]-phenyl ester A 1.0 g sample of 60% NaH in oil was placed into a flask and washed with hexanes. The NaH was suspended in 20 mL of $CH_2Cl_2$ and cooled in an ice bath. A sample of 3-[(1-RS, 2-RS)-2-[(dimethylamino)methyl]-1-hydroxycyclohexyl]-phenol (6.3 g, 0.024 mol) in $CH_2Cl_2$ (20 mL) was added. After stirring for 1 h, a solution triflic anhydride (6 mL in 10 mL $CH_2Cl_2$) was added dropwise. The ice bath was removed and the reaction was stirred at room temperature for 2 h. The reaction was then washed with water, brine, and dried ($Na_2SO_4$). The solvent was evaporated to give 11 g of an oil. The residue was passed through a silica gel column (4:1, $CH_2Cl_2$:MeOH) to give 7.9 g (83%) of trifluoromethanesulfonic acid 3-[(1-RS, 2-RS)-2-[(dimethylamino)methyl]-1-hydroxycyclohexyl]-phenyl ester. MS m/z=233 (M-OTf).

Procedure C

Methyl 3-[(1-RS, 2-RS)-[(2-dimethylamino)methyl]-1-hydroxycyclohexyl]-benzoate

Into a pressure bottle was placed trifluoromethanesulfonic acid 3-[(1-RS, 2-RS)-2-[(dimethylamino)methyl]-1-hydroxycyclohexyl]-phenyl ester (6.8 g, 0.018 mol), DMF (130 mL), MeOH (54 mL), DPPF (380 mg, 8 mol %), Pd(OAc)$_2$ (163 mg, 4 mol %), and TEA (5.4 mL). Gaseous carbon monoxide was bubbled through the reaction mixture for 5 min and the bottle was closed and heated to 100° C. for 2 h. Upon cooling, the reaction was poured into water and extracted with 70:30 Et$_2$O/EtOAc (3×). The organic portions were combined, washed with water, brine, dried (Na$_2$SO$_4$), and filtered. The solvent was evaporated in vacuo and the residue was passed through a silica gel column (90:10:1 CH$_2$Cl$_2$: MeOH: NH$_4$OH) to give 2.5 g (48%) of the title compound. MS m/z=292 (MH$^+$)$^;$ $^1$H NMR (CDCl$_3$) δ 8.2-7.4 (Ar, 4H); 3.9 (s, 3H); 2.3 (d, 1H); 2.1 (s, 6H); 1.9-1.3 (m, 10H).

Procedure D

3-[(1-RS, 2-RS)-[(2-Dimethylamino)methyl]-1-hydroxycyclohexyl]-benzoic acid

A sample of methyl 3-[(1-RS, 2-RS)-2-[(dimethylamino)methyl]-1-hydroxycyclohexyl]-benzoate (2.5 g, 8.6 mmol), MeOH (20 mL), and 3N NaOH (9 mL) were refluxed for 1.5 h. The MeOH was evaporated in vacuo and the residue was made acidic with HCl (conc). The solvent was evaporated in vacuo and the residue triturated with Et$_2$O. The solid was dried overnight in vacuo to give 2.2 g (92%) 3-[(1-RS, 2-RS)-2-[(dimethylamino)methyl]-1-hydroxycyclohexyl]-benzoic acid.

Example 5

3-[(1-RS, 2-RS)-2-[(dimethylamino)methyl]-1-hydroxycyclohexyl]-N,N-diethyl-benzamide, Cpd 5

A sample of 3-[(1-RS, 2-RS)-2-[(dimethylamino)methyl]-1-hydroxycyclohexyl]-benzoic acid (0.1 g, 0.36 mmol), CH$_2$Cl$_2$ (5 mL), and diethylamine (0.08 mL, 0.36 mmol) was placed into a flask and stirred for 5 min. To the reaction was added HATU (0.13 g, 0.36 mmol) and stirring was continued for 2 h. Water was added and the organic phase was separated, washed again with water, dried (Na$_2$SO$_4$), and filtered. The filtrate was evaporated in vacuo and the residue passed through a silica gel column (90:10:1, CH$_2$Cl$_2$: MeOH: NH$_4$OH) to give 42 mg (35%) of 3-[(1-RS, 2-RS)-2-[(dimethylamino)methyl]-1-hydroxycyclohexyl]-N,N-diethyl-benzamide: MS m/z=333 (MH$^+$)$^;$ $^1$H NMR (CDCl$_3$) δ 7.7-7.2 (Ar, 4H), 3.6 and 3.2 (bq, 4H), 2.4 (dd, 1H), 2.1 (s, 6H), 2.0-1.5 (m, 10H), 1.1 (bt, 6H).

Example 6

N-Cyclopropyl-3-[(1-RS, 2-RS)-2-[(dimethylamino)methyl]-1-hydroxycyclohexyl]-benzamide, Cpd 6

Using the procedure of Example 5, substituting cyclopropylamine for diethylamine, the title compound was prepared in 45% yield. MS m/z=317 (MH$^+$)$^;$ $^1$H NMR (CDCl$_3$) δ 7.7-7.2 (Ar, 4H); 2.1 (s, 6H); 2.0-1.5 (m, 12H); 0.5 (2t, 4H).

Example 7

3-[(1-RS, 2-RS)-2-[(Dimethylamino)methyl]-1-hydroxycyclohexyl]-N-methylbenzamide Using the procedure of Example 5, substituting N-methylamine for diethylamine, the title compound was prepared in 37% yield. MS m/z=291 (MH$^+$)$^;$ $^1$H NMR (CDCl$_3$) δ 7.7-7.2 (Ar, 4H), 2.9 (d, 3H); 2.1 (s, 6H), 2.3-1.5 (m, 10H).

Compounds 1 through 7 of Formula (I) in Table 1 were synthesized using the procedures described above.

TABLE 1

| Cpd No. | |
|---|---|
| 1 | 3-[(1-RS,2-SR)-2-[(dimethylamino)methyl]-1-hydroxycyclohexyl]-benzamide |
| 2 | 3-[(1-RS,2-RS)-2-[(dimethylamino)methyl]-1-hydroxycyclohexyl]-benzamide |
| 3 | (−)-3-[(1R,2R)-rel-2-[(dimethylamino)methyl]-1-hydroxycyclohexyl]-benzamide |
| 4 | (+)-3-[(1S,2S)-rel-2-[(dimethylamino)methyl]-1-hydroxycyclohexyl]-benzamide |
| 5 | 3-[(1-RS,2-RS)-2-[(dimethylamino)methyl]-1-hydroxycyclohexyl]-N,N-diethyl-benzamide |
| 6 | N-cyclopropyl-3-[(1-RS,2-RS)-2-[(dimethylamino)methyl]-1-hydroxycyclohexyl]-benzamide |
| 7 | 3-[(1-RS,2-RS)-2-[(dimethylamino)methyl]-1-hydroxycyclohexyl]-N-methylbenzamide |

Biological Examples

Example 1

Rat Brain Mu and Delta Opioid Receptor Binding Assay

The activity of compounds of the invention as opioids is demonstrated by the rat brain mu and delta opioid receptor binding assay as described below.

Procedure

Male, Wistar rats (150-250 g, VAF, Charles River, Kingston, N.Y.) were killed by cervical dislocation and their brains removed and placed immediately in ice cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in Tris buffer in a Teflon®-glass homogenizer. The homogenate was diluted to a concentration of 1 g of forebrain tissue per 100 mL Tris buffer and centrifuged at 39,000×G for 10 min. The pellet was resuspended in the same volume of Tris buffer with several brief pulses from a Polytron homogenizer. This particulate preparation was used for the opioid receptor binding assays. Following incubation with the mu opioid selective peptide ligand [$^3$H]DAMGO or the delta opioid selective ligand [$^3$H]DPDPE at 25° C., the tube contents were filtered through Whatman GF/B filter sheets on a Brandel cell harvester. The tubes and filters were rinsed three times with 4 mL of 10 mM HEPES (pH 7.4) and the radioactivity associated with the filter circles determined using Formula 989 scintillation fluid (New England Nuclear, Boston, Mass.) in a scintillation counter.

Analysis

The data were used to calculate a $K_i$ value, using GraphPad Prism.

Example 2

[$^{35}$S]GTPγS Binding Assay in Human mu opioid-CHO Cell Membranes

Preparation of Membranes

Human mu-CHO cell membranes were purchased from Receptor Biology, Inc. (Baltimore, Md.). About 10 mg/ml of membrane protein was suspended in 10 mM TRIS-HCl, pH 7.2, 2 mM EDTA, 10% sucrose.

Membranes were maintained at 4-8° C. 1 ml of membranes was added into 15 ml cold assay buffer, containing 50 mM HEPES, pH 7.6, 5 mM MgCl$_2$, 100 mM NaCl, 1 mM DTT and 1 mM EDTA. The membrane suspension was homogenized with a Polytron 2 times and centrifuged at 3000 rpm for 10 min. The supernatant was then centrifuged at 18,000 rpm for 20 min. The pellet was resuspended in 10 ml assay buffer with a Polytron.

Incubation Procedure

The pellet membranes (20 μg/ml) were preincubated with Scintillation Proximity Assay beads (SPA, 10 mg/ml) at 25° C. for 45 min in the assay buffer. The SPA beads (5 mg/ml) coupled with membranes (10 μg/ml) were then incubated with 0.5 nM [$^{35}$S]GTPγS in the same HEPES buffer containing 50 μM GDP in total volume of 200 μl. A range of concentrations of receptor agonists were used to stimulate [$^{35}$S] GTPγS binding. The basal binding was tested in the absence of agonist and non-specific binding was tested in the presence of 10 μM unlabeled GTPγS. Radioactivity was quantified on a Packard TopCount.

Data

Data were Calculated as Follows:

% of basal=(stimulated−non-specific)*100/(basal−non specific)

% Inhibition=(% Basal of 1 μM DAMGO−% Basal of compound)*100/(% Basal of 1 μM DAMGO−100)

[$^{35}$S]GTPγS Binding Assay in NG108-15 Cell Membrane

Preparation of Membranes

NG108-15 cell membranes were purchased from Applied Cell Sciences (Rockville, Md.). An 8 mg/mL portion of membrane protein was suspended in 10 mM TRIS-HCl, pH 7.2, 2 mM EDTA, 10% sucrose.

Membranes were maintained at 4-8° C. A 1 mL portion of membranes was added into 10 mL cold assay buffer, containing 50 mM Tris, pH 7.6, 5 mM MgCl$_2$, 100 mM NaCl, 1 mM DTT and 1 mM EGTA. The membrane suspension was homogenized with a Polytron 2 times and centrifuged at 3000 rpm for 10 min. The supernatant was then centrifuged at 18,000 rpm for 20 min. The pellet was resuspended in 10 ml assay buffer using a Polytron.

Incubation Procedure

The pellet membranes (75 μg/ml) were preincubated with SPA beads (10 mg/ml) at 25° C. for 45 min in the assay buffer. The SPA beads (5 mg/ml) coupled with membranes (37.5 μg/ml) were then incubated with 0.1 nM [$^{35}$S] GTPγS in the same Tris buffer containing 100 μM GDP in total volume of 200 μl. A range of concentrations of receptor agonists was used to stimulate [$^{35}$S] GTPγS binding. The basal binding was tested in the absence of agonist and non-specific binding was tested in the presence of 10 μM unlabeled GTPγS. The radioactivity was quantified on a Packard TopCount.

Data

Calculations were performed as follows:

% of Basal=(stimulated−non specific)*100/(basal−non specific).

$EC_{50}$ values were calculated using the Prism program.

TABLE 2

| | In vitro mu and delta opioid receptor parameters | | | |
|---|---|---|---|---|
| Cpd No. | Mu opioid binding Ki (nM) | Delta opioid binding Ki (nM) | Mu opioid GTPγS ($EC_{50}$/ relative efficacy) | Delta opioid GTPγS ($EC_{50}$, nM) |
| 1 | 1387 | 9875 | | |
| 2 | 29.43 | 2470 | Agonist | 5630 |
| 3 | 15.48 | 3141 | 167 nM/75% | |
| 4 | 828 | >10,000 | 4820 nM/41% | |
| 5 | >10,000 | >10,000 | | |
| 6 | 5189 | >10,000 | | |
| 7 | 2121 | >10,000 | | |

Example 3

Rat CFA Radiant Heat Model of Inflammatory Pain

Intraplantar injection of Complete Freund's Adjuvant (CFA) in rodents results in a strong, long-lasting inflammatory reaction, characterized by a chronic and pronounced hyperalgesia to both thermal and mechanical stimuli. These effects peak between 24-72 h following injection, and can last for several days to a few weeks. To assess the ability of compounds to reverse thermal hyperalgesia, male Sprague-Dawley rats (200-350 g) were given an intraplantar injection of CFA (1:1 CFA:saline, 100 μL) into their left hindpaw. Following a 24-h incubation period, response latencies on the Radiant Heat Paw Stimulator (RH) were obtained and compared to baseline (pre-CFA) latencies. The RH device automatically registered lifting of the paw from the surface of the glass. Only rats that exhibited at least a 25% reduction in response latency from baseline (i.e. hyperalgesia) were included in further analysis. Following the post CFA latency assessment, rats were dosed orally (2.5 mL/kg) with test compound or vehicle (hydroxypropylmethylcellulose, HPMC). Percent reversal of hyperalgesia was calculated for each animal as (Treatment Response−postCFA Response)/ (preCFA Response−postCFA Response)×100. Therefore, a return to normal pre-CFA thresholds was defined as 100% efficacy, whereas no change from post-CFA thresholds was 0% efficacy. Average % reversal of hyperalgesia was then calculated for each treatment group (n=6-8 rats/group). The Compounds 3 and 4 were antihyperalgesic in this model (see FIG. 1).

Example 4

Spinal Nerve Ligation (SNL) Model of Neuropathic Pain

Animals:

Male Sprague Dawley rats weighing 145 to 165 g (approximately 6 weeks of age) were obtained from Harlan (Indianapolis, Ind.). Food and water were provided ad lib and a 12 h light and 12 h dark cycle were maintained. Animals were group housed under specific pathogen-free, barrier maintained environment and were allowed to acclimate for no less than 1 week. Following surgery, animals were housed individually in solid bottom polycarbonate cages with automatic watering devices at 22° C. and a relative humidity of 60%. All animals received Harland Tekland Diet # 8604.

Surgery:

Anesthesia was induced using isoflurane (IsoVet™) inhalant in an induction chamber (3-5% in 2 L/min of $O_2$). Once recumbent, the animal was removed and placed into a nose cone which delivered inhalant isoflurane (0.5-2.5% at 2 L/min Of $O_2$). The dorsal pelvic area was shaved and scrubbed aseptically with chlorhexidine scrub, 70% alcohol, and a 5% chlorhexidine solution. The animal was held in ventral recumbency on a heating pad, and the surgical procedure described by Kim and Chung (1992) was performed. The left paraspinal muscles were separated from the spinous processes at the level of Lumbar 4 to Sacral 2 (L4-S2). Once the musculature was retracted, the L6 transverse process was removed using a small rongeur. L4 and L5 spinal nerves could then be visualized. L5 was then isolated and ligated using 6-0 silk suture material. Warm saline and a dose of long-acting antibiotic was administered immediately post-op before recovery form anesthesia.

Evaluation of Mechanical Allodynia:

At least one week following surgery, animals were individually placed in a Lucite testing chamber with a wire mesh bottom. Mechanical (tactile) allodynia was measured by recording the pressure at which the affected paw was withdrawn from graded stimuli (Von Frey hairs ranging from 4.0 to 148.1 mN equivalent to 0.25 to 15 g of pressure) applied to the plantar surface of the paw (between the footpads) according to the procedure of Chaplan et. al (1994) in order to calculate paw withdrawal threshold (PWT). Normal rats can withstand at least 15 g of pressure without responding. SNL rats can respond to as little as 0.25 g of pressure. Rats were included in this study only if their PWT was below 4.0 g.

Von Frey Testing of Compounds:

Animals were used for compound testing between 2 weeks and 8 weeks post-operatively. Animals were always pre-tested for baseline withdrawal threshold on the day of testing. Following a 16 h fast, PWT was evaluated at 30 min, 1 h, 2 h, and 4 h post-dosing. Dose-response studies were conducted at the time of peak effect. Studies were conducted in a blinded manner.

Statistical Analysis:

Data were normalized and results were presented as % MPE (maximum possible effect) of the drug.

$$\% \ MPE = \frac{x \ g/\text{force} - \text{baseline } g/\text{force}}{15 \ g/\text{force} - \text{baseline } g/\text{force}} \times 100$$

The effect of example compounds is presented in Table 3, and Cpd 3 had an $ED_{50}$ value of 17 mg/kg at 2 h (see FIG. 2).

TABLE 3

Effect of compounds in spinal nerve ligation model

| Cpd No. | Dose | MPE or $ED_{50}$ value |
|---|---|---|
| 2 | 3 mg/kg, i.v. | 87% |
| 2 | 30 mg/kg, p.o. | 88% |
| 3 | — | $ED_{50}$ = 17 mg/kg |
| 4 | 30 mg/kg, p.o. | 39% |
| 4 | 100 mg/kg, p.o. | 95% |

Example 5

Investigation of Tolerance Development

The development of tolerance to the analgesic effect of mu opioid compounds is well known. The development of tolerance to the antiallodynic effect of the Compound 3 was investigated by administering the compound to spinal nerve ligated rats for five days. The antiallodynic effect of the compound was evaluated on days one and five. Dosing for five days did not diminish the antiallodynic effect of the compound; compound effect was the same or was slightly increased by repeated dosing (see FIG. 3).

In contrast, tolerance to the antiallodynic effect of the typical mu opioid morphine rapidly developed, little or no antiallodynic effect remaining after five days of dosing (see FIG. 4).

Example 6

Metabolic Stability

The metabolic stability of Compound 3 was investigated using several approaches. The compound was incubated with liver microsomes from mouse, rat, dog and human and the percent of compound remaining after ten min quantified. The compound was metabolically robust in all species tested. Notably, no metabolism of the compound was observed under these test conditions in human liver microsomes.

TABLE 4

In vitro metabolic stability of Cpd 3 in several species (% of Cpd remaining after 10 min incubation with liver microsomes).

| Species | % remaining after 10 min |
|---|---|
| Mouse | 88.2 |
| Rat | 94.5 |
| Dog | 92.6 |
| Human | 101.4 |

In a follow up study in human liver microsomes, the percent of compound remaining was determined at several incubation times (30, 60 and 90 min). The in vitro half life of the compound was determined to be >100 minutes.

In a study using recombinant human P450 isoforms, the compound was only a weak inhibitor ($IC_{50}$>10 μM) of all isoforms tested, 3A4, 2D6, 2C9, 2C19, and 1A2.

In an in vitro study using human liver microsomes, no glucuronidation of the compound was detected.

Taken together, these several in vitro metabolism studies point to the unusual metabolic stability of the compound.

What is claimed is:

1. A method for treatment of pain in a subject in need thereof comprising administering to the subject a therapeutically effective amount of a compound selected from the group consisting of:
- 3-[(1-RS, 2-SR)-2-[(dimethylamino)methyl]-1-hydroxycyclohexyl]-benzamide;
- 3-[(1-RS, 2-RS)-2-[(dimethylamino)methyl]-1-hydroxycyclohexyl]-benzamide;
- (−)-3-[(1R, 2R)-rel-2-[(dimethylamino)methyl]-1-hydroxycyclohexyl]-benzamide;
- (+)-3-[(1S, 2S)-rel-2-[(dimethylamino)methyl]-1-hydroxycyclohexyl]-benzamide;
- 3-[(1-RS, 2-RS)-2-[(dimethylamino)methyl]-1-hydroxycyclohexyl]-N,N-diethylbenzamide;
- N-cyclopropyl-3-[(1-RS, 2-RS)-2-[(dimethylamino)methyl]-1-hydroxycyclohexyl]-benzamide; and
- 3-[(1-RS, 2-RS)-2-[(dimethylamino)methyl]-1-hydroxycyclohexyl]-N-methylbenzamide.

2. The method of claim 1, wherein the compound is selected from the group consisting of:
- (−)-3-[(1R, 2R)-rel-2-[(dimethylamino)methyl]-1-hydroxycyclohexyl]-benzamide and
- (+)-3-[(1S, 2S)-rel-2-[(dimethylamino)methyl]-1-hydroxycyclohexyl]-benzamide;

3. A pharmaceutical composition comprising a compound selected from the group consisting of:
- 3-[(1-RS, 2-SR)-2-[(dimethylamino)methyl]-1-hydroxycyclohexyl]-benzamide;
- 3-[(1-RS, 2-RS)-2-[(dimethylamino)methyl]-1-hydroxycyclohexyl]-benzamide;
- (−)-3-[(1R, 2R)-rel-2-[(dimethylamino)methyl]-1-hydroxycyclohexyl]-benzamide;
- (+)-3-[(1S, 2S)-rel-2-[(dimethylamino)methyl]-1-hydroxycyclohexyl]-benzamide;
- 3-[(1-RS, 2-RS)-2-[(dimethylamino)methyl]-1-hydroxycyclohexyl]-N,N-diethylbenzamide;
- N-cyclopropyl-3-[(1-RS, 2-RS)-2-[(dimethylamino)methyl]-1-hydroxycyclohexyl]-benzamide; and
- 3-[(1-RS, 2-RS)-2-[(dimethylamino)methyl]-1-hydroxycyclohexyl]-N-methylbenzamide.

4. The composition of claim 3 wherein the compound is selected from the group consisting of:
- (−)-3-[(1R, 2R)-rel-2-[(dimethylamino)methyl]-1-hydroxycyclohexyl]-benzamide and
- (+)-3-[(1S, 2S)-rel-2-[(dimethylamino)methyl]-1-hydroxycyclohexyl]-benzamide.

* * * * *